United States Patent [19]

Shimizu

[11] Patent Number: 4,604,653
[45] Date of Patent: Aug. 5, 1986

[54] DOCUMENT FILING SYSTEM

[75] Inventor: Makoto Shimizu, Tokyo, Japan

[73] Assignee: Tokyo Shibaura Denki Kabushiki Kaisha, Kawasaki, Japan

[21] Appl. No.: 543,964

[22] Filed: Oct. 20, 1983

[30] Foreign Application Priority Data

Oct. 21, 1982 [JP] Japan .................. 57-185126
Oct. 27, 1982 [JP] Japan .................. 57-188623

[51] Int. Cl.⁴ ............... H04N 1/00; H04N 1/32; H04N 1/40
[52] U.S. Cl. .................... 358/256; 358/257; 358/280; 364/518
[58] Field of Search ........... 358/256, 257, 280, 310, 358/311, 296; 364/518, 523

[56] References Cited

U.S. PATENT DOCUMENTS

| | | | |
|---|---|---|---|
| 4,196,450 | 4/1980 | Miller et al. | 358/256 |
| 4,437,127 | 3/1984 | Hirose | 358/257 |
| 4,445,195 | 4/1984 | Yamamoto | 364/900 |
| 4,485,411 | 11/1984 | Yamamoto | 364/518 |
| 4,490,747 | 12/1986 | Yokoyama | 358/296 |
| 4,491,874 | 1/1985 | Yamamoto | 358/296 |
| 4,498,107 | 2/1985 | Yoshimaru et al. | 358/256 |
| 4,499,500 | 2/1985 | Nagashima | 358/280 |
| 4,500,926 | 2/1985 | Yoshimaru | 358/256 |

FOREIGN PATENT DOCUMENTS

| | | |
|---|---|---|
| 0051226 | 12/1982 | European Pat. Off. |
| 3311663 | 10/1983 | Fed. Rep. of Germany |
| 3338385 | 5/1984 | Fed. Rep. of Germany |
| 7634527 | 7/1977 | France |
| 1487507 | 10/1977 | United Kingdom |

OTHER PUBLICATIONS

"Megadoc, a Modular System for Electronic Document Handling" by J. A. deVos, *Philips Technical Review*, vol. 39, 1980, No. 12, pp. 329–343.

Primary Examiner—James J. Groody
Assistant Examiner—John K. Peng
Attorney, Agent, or Firm—Cushman, Darby & Cushman

[57] ABSTRACT

Items of identification data corresponding to the groups of items of image information which are stored in an optical disk are stored in a floppy disk. Before any group of items of image information is retrieved from the optical disk, the identification data corresponding to this group is displayed by a CRT display device.

21 Claims, 22 Drawing Figures

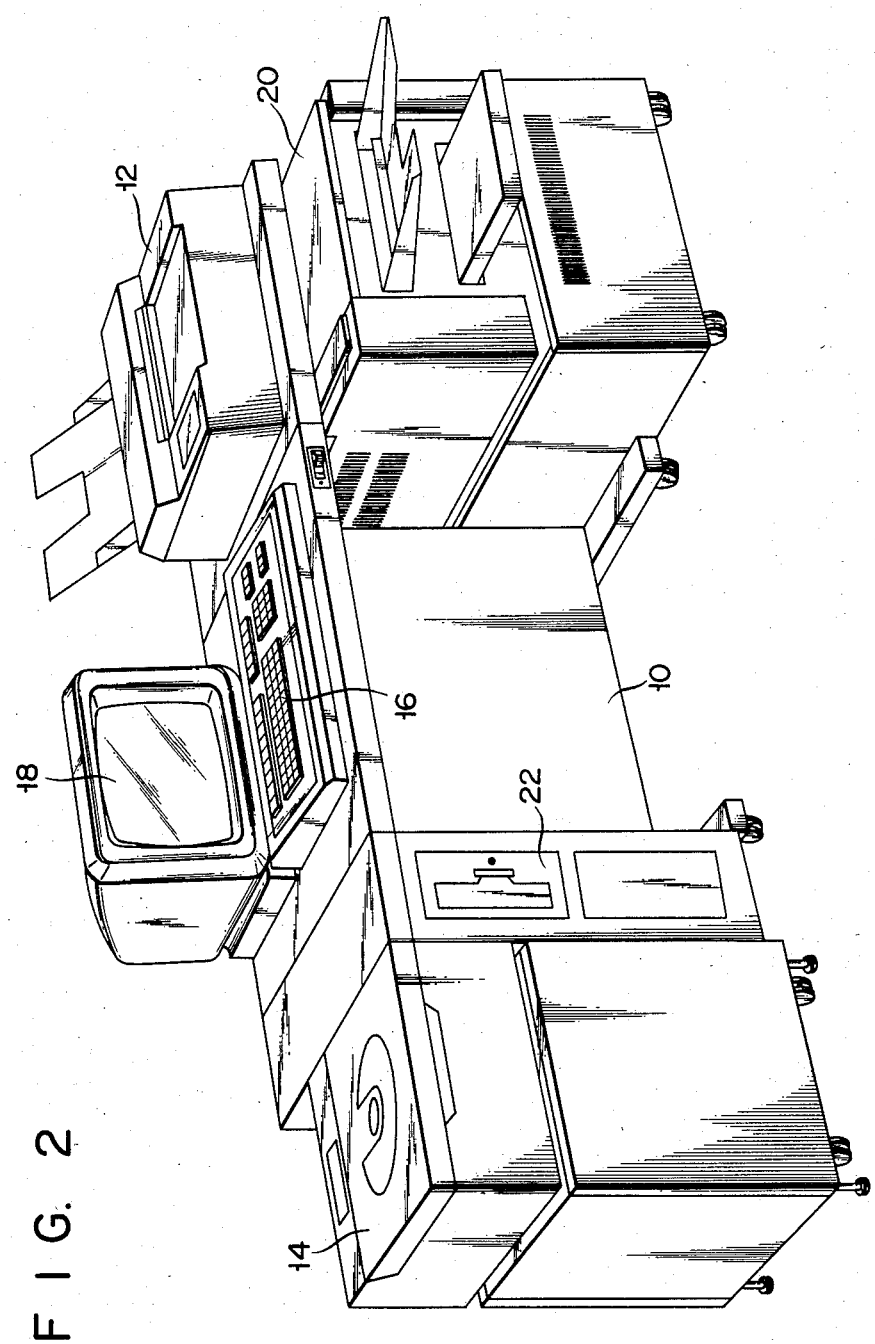

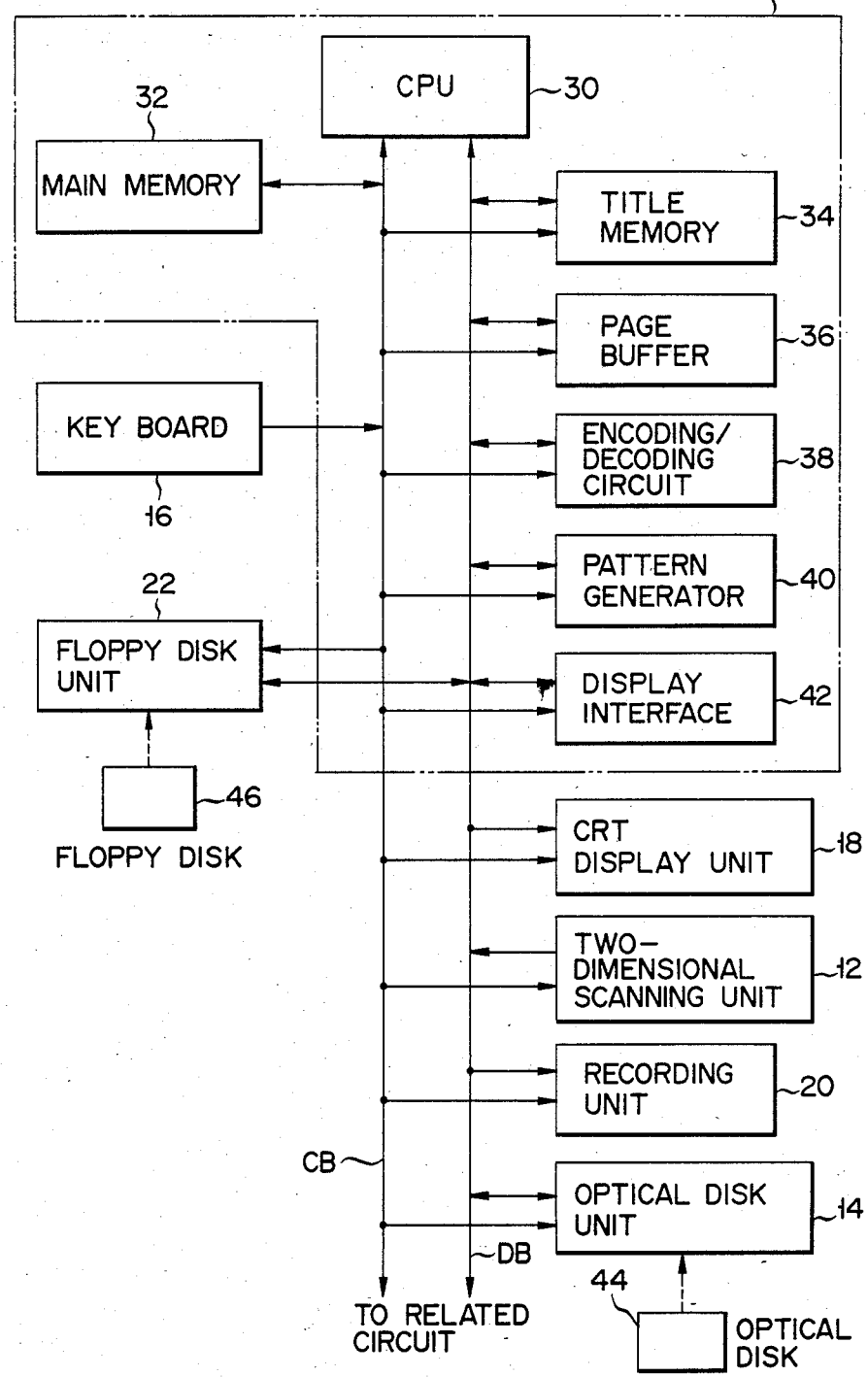

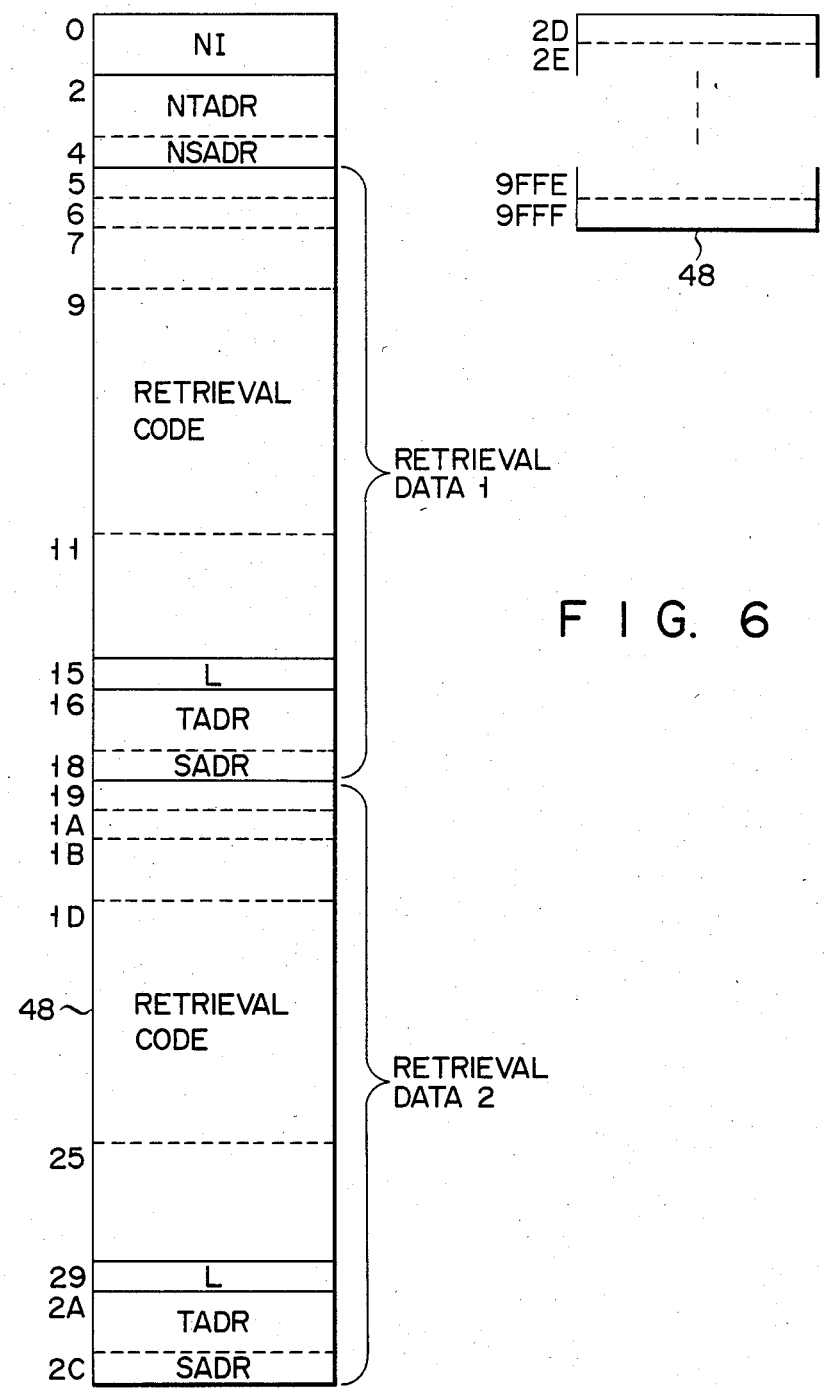
F I G. 6

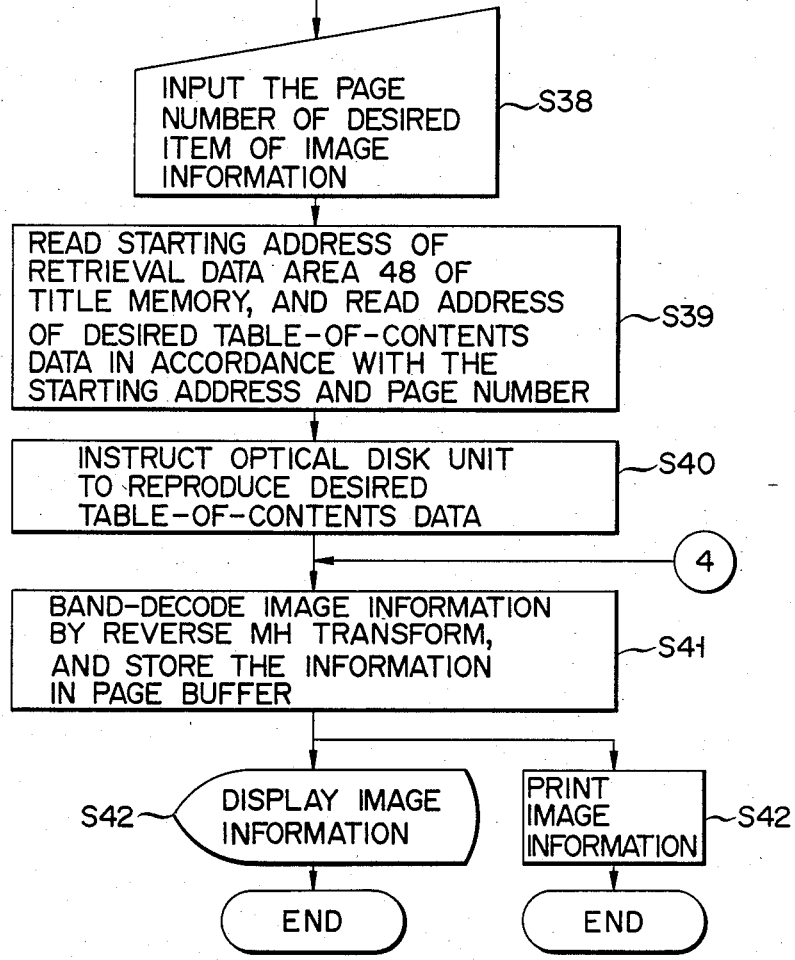
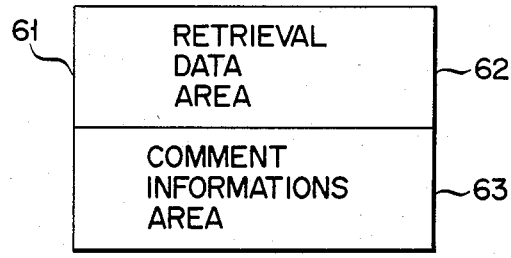

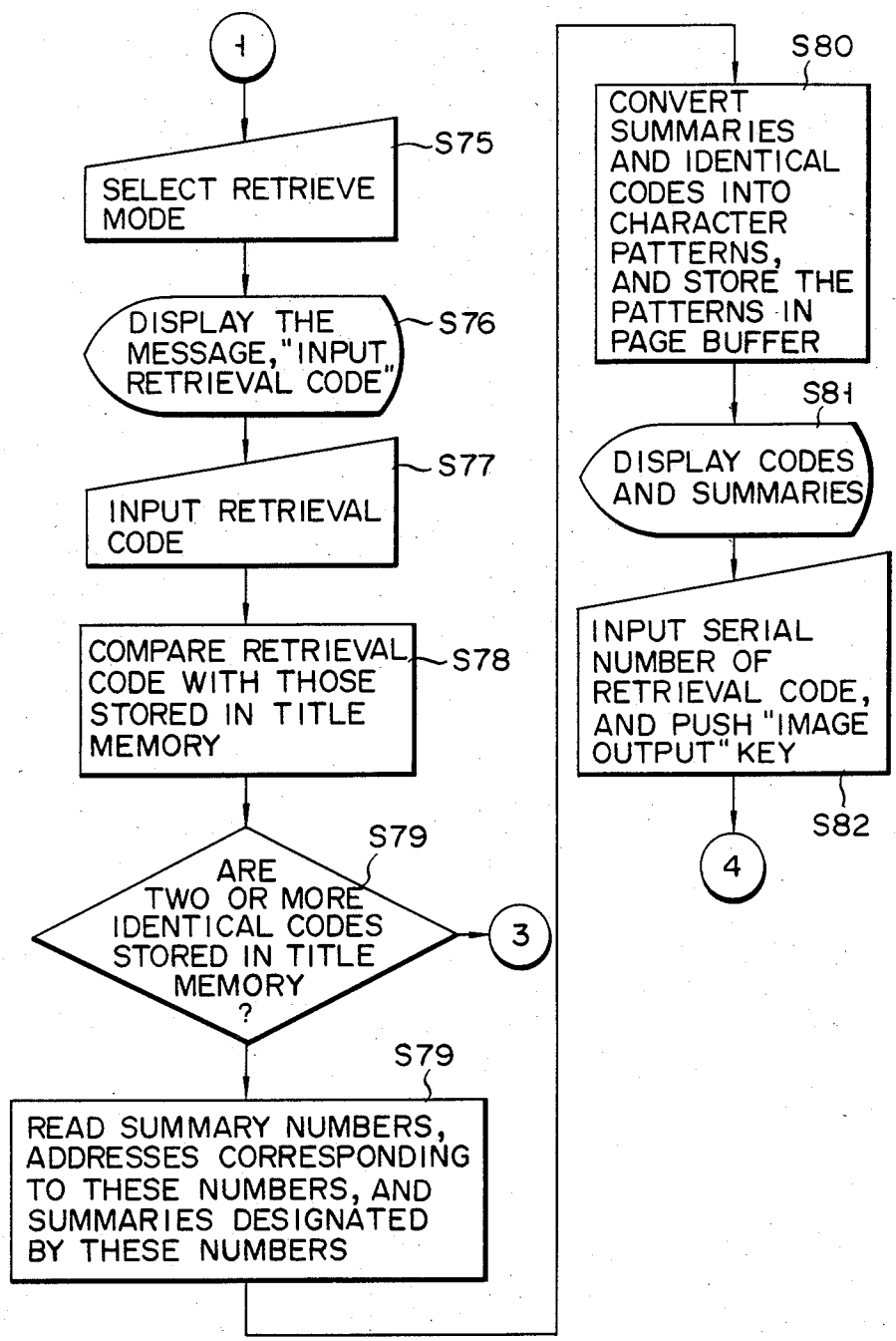

DOCUMENT FILING SYSTEM

BACKGROUND OF THE INVENTION

The present invention relates to a document filing system wherein items of image information, e.g., text data, are successively stored in an optical disk, retrieval data corresponding to the image information is stored in a floppy disk and the image information is read from the optical disk in accordance with the retrieval data.

Recently a document filing system has been developed and put to a practical use. This system reads a great amount of image information, e.g., text data, by means of two-dimensional optical scanning and stores the information in a storage, e.g., an optical disk. The system also stores retrieval data corresponding to the image information in another storage, e.g., a floppy disk. To retrieve the image information from the optical data, an operator inputs the retrieval data by operating a keyboard. Then, the retrieval data is displayed by a CRT display. If the operator finds this data correct, he operates the keyboard to input the number of the desired page of the text data. The desired page of text data is then displayed by the CRT display and/or visually output by an output device, e.g., a printer.

Any retrieval data displayed by the CRT display is too brief for the operator to identify it with the corresponding image information correctly. In other words, the operator may not be sure if the retrieval data is correct, unless the text data is displayed, page by page, and he scrutinizes each page. This method of judging whether or not each retrieval data is correct is very time-consuming.

SUMMARY OF THE INVENTION

The object of the present invention is to provide a document filing system with which an operator can easily and quickly judge whether or not any retrieval data that he has input is correct, without operating a keyboard many times.

According to the present invention, there is provided a document filing system wherein groups of image information items are stored in a first storage, items of retrieval data corresponding to the items of image information are stored in a second storage, and each item of retrieval data is retrieved before the corresponding item of image information is output.

Further, according to the invention, there is provided a document filing system wherein items of image information are stored in a first storage, the summaries of these items are stored in a second storage, and the summary of any item of image information is read before this item is retrieved.

BRIEF DESCRIPTION OF THE DRAWINGS

FIG. 3 is a block diagram of the document filing system of FIG. 1;

FIG. 6 illustrates how items of information for administrating image information are stored in a storage area of the floppy disk;

FIGS. 8A-1 to 8D are flow charts illustrating the operations of the system shown in FIG. 1;

FIG. 9 shows the storage areas of a floppy disk used in a second document filing system of a second embodiment according to the present invention;

FIGS. 12A-1 to 12E are flow charts illustrating the operation of the second document filing system of the second embodiment according to the present invention.

DETAILED DESCRIPTION OF THE PREFERRED EMBODIMENTS

Figure 1:
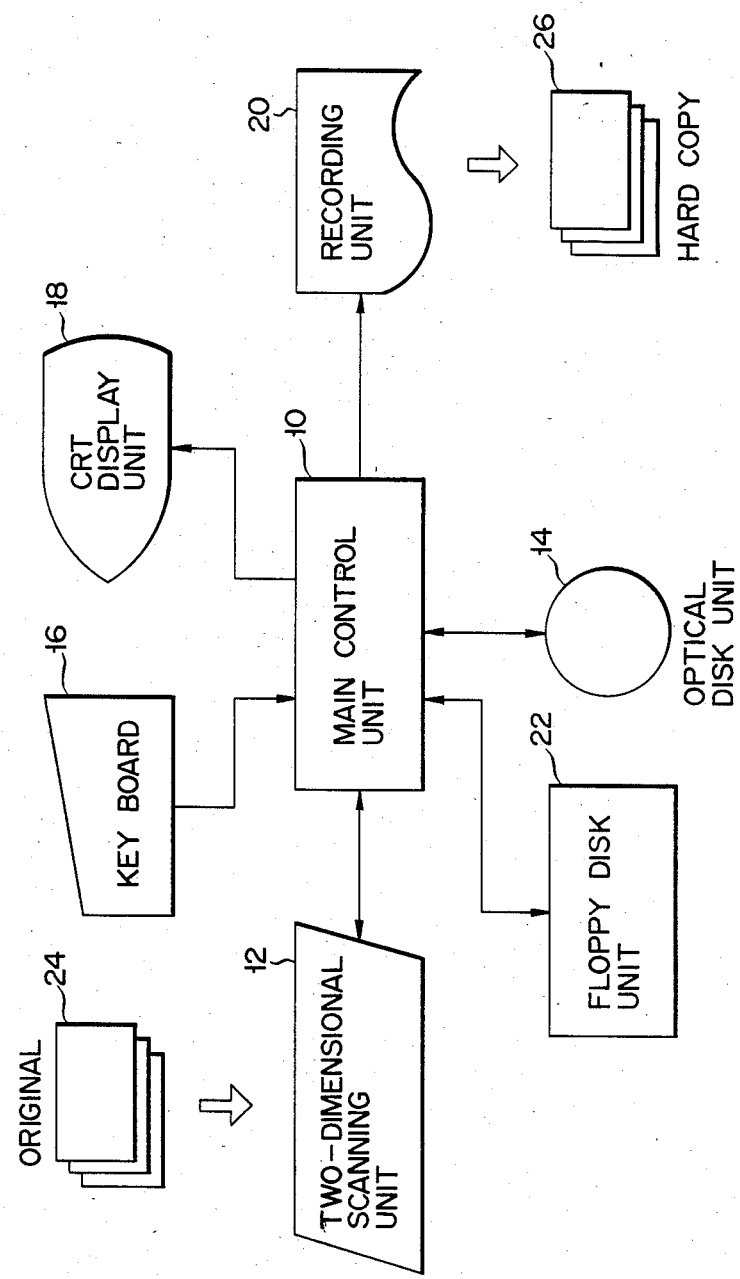
FIG. 1 is a graphical representation of a document filing system of a first embodiment according to the present invention.
Figures 1, 8A:
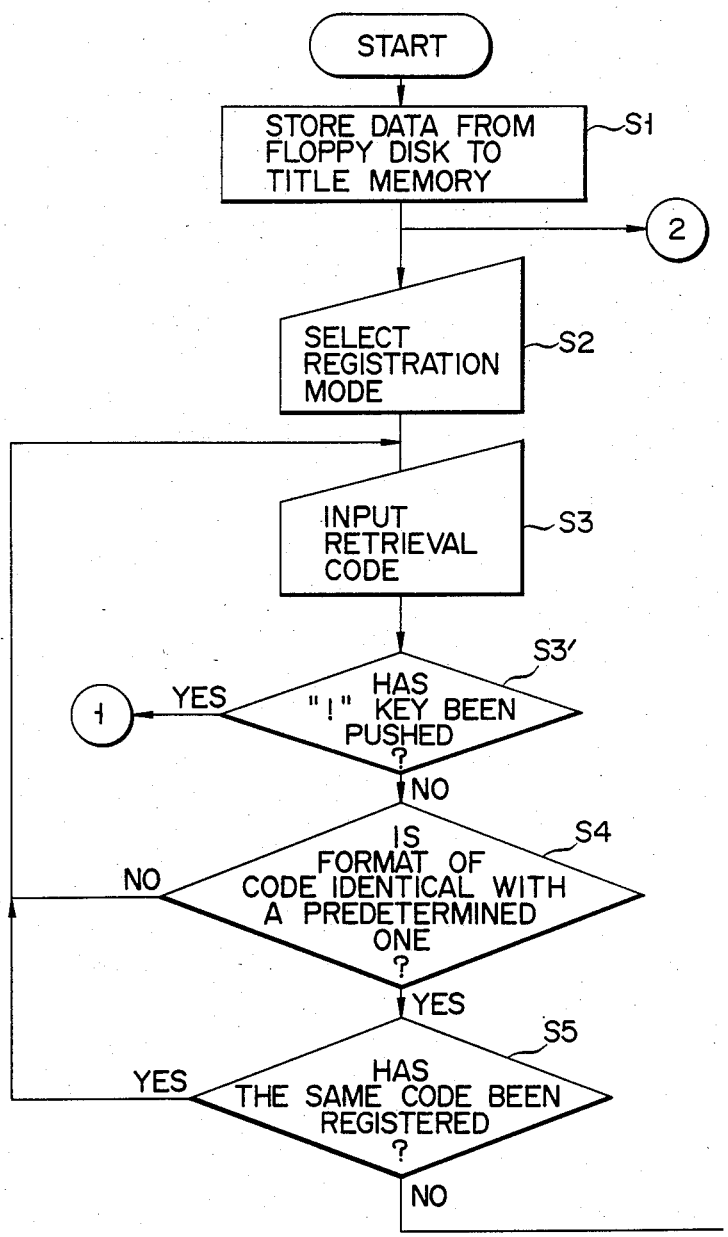
Figures 2, 8A:
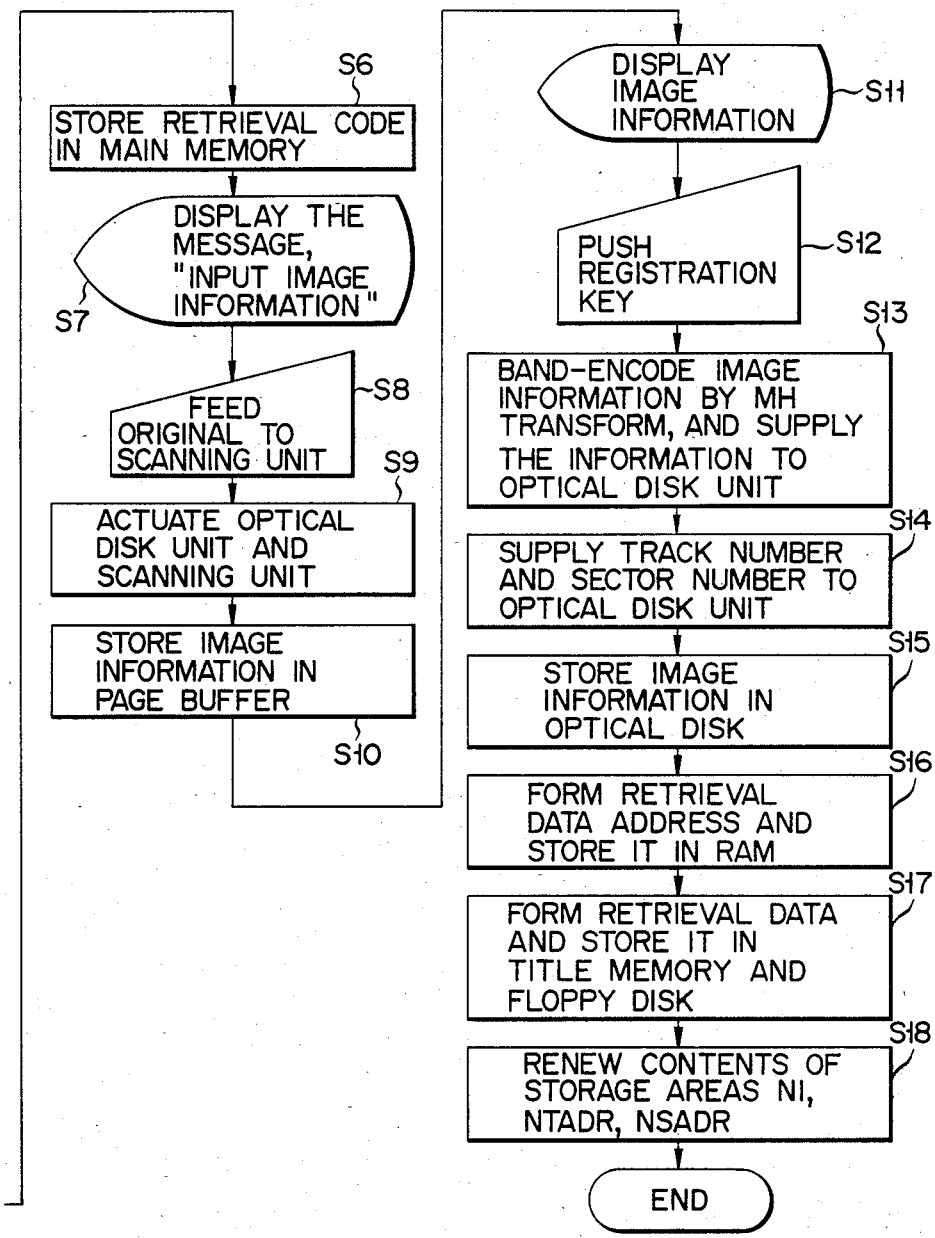
Figure 8B:
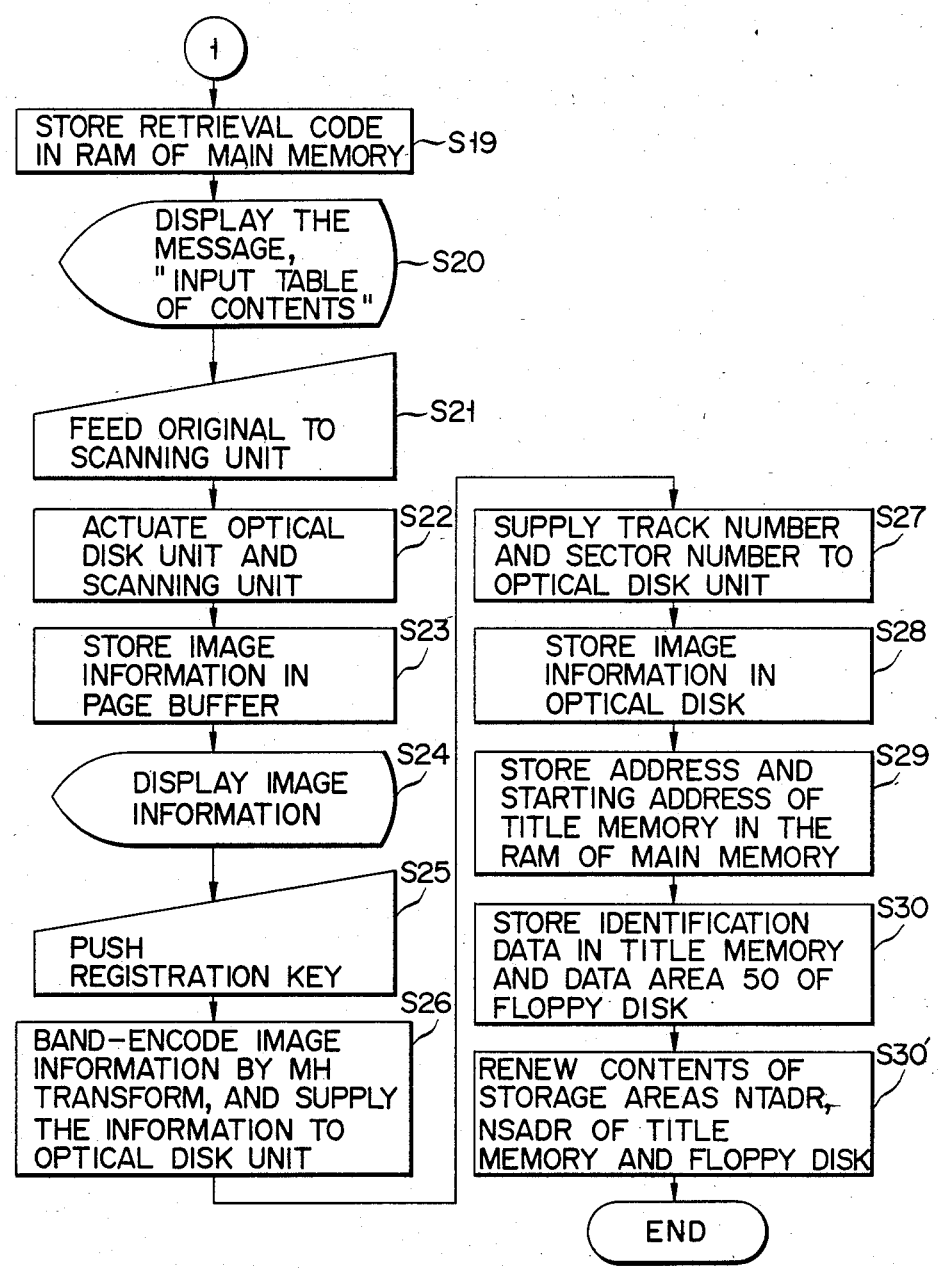

FIGS. 1 and 2 show a document filing system of a first embodiment according to the present invention. A main control unit 10 is connected to a two-dimensional scanning unit 12, an optical disk unit 14, a keyboard 16, a CRT display unit 18, a recording unit 20 and a floppy disk unit 22. The unit 10 includes a microprocessor and processes image information and retrieval data in various manners, as will be described later. The two-dimensional scanning unit 12, which is used as a reading unit, scans an original 24 with a laser beam in two directions at right angles and produces electric signals corresponding to the image information printed on the original 24. The image information, i.e., the electric signals, is supplied through the main control unit 10 to the optical disk unit 14 and stored in an optical disk (i.e., a first storage). The keyboard 16 is used to input a retrieval code of the image information, various instructions, table-of-contents data, titles of the items of this data, etc. The CRT display unit 18, which is used as an output device displays the image information supplied from the scanning unit 12 via the main control unit 10. It may also display image information read from the optical disk unit 14 and supplied through the unit 10. It may display retrieval codes, a table-of-contents data, titles of the items of this data, etc. supplied from the keyboard 16 or the floppy disk unit 22. The recording unit 20 is another output device and outputs the image information from the scanning unit 12 or optical disk unit 14 in the form of hard copy 26. The floppy disk unit 22 receives retrieval data from the main control unit 10. The retrieval data corresponds to image information and consists of a retrieval code input through the keyboard 16 and data representing the address of the image information stored in the optical disk. The floppy disk unit 22 also receives identification data from the unit 10. The identification data corresponds to an image information group. This information is input through the keyboard 16 and includes table-of-contents data and titles of the items of this data. The floppy disk unit 22 stores the retrieval data and indentification data in a floppy disk.

FIG. 3 is a block diagram of the main control unit 10 and also shows the other of the document filing system of FIG. 1.

The main control unit 10 comprises a CPU 30 for performing various controls and a main memory 32 including a ROM (read only memory) storing control programs and a RAM (random access memory) used as an internal memory for data processing. The unit 10 further comprises a title memory 34 for storing retrieval data read from, or to be written in, the floppy disk 46, a page buffer 36 capable of storing at least one unit of image information, e.g., one page of the original 24, an encoding/decoding circuit 38 for band-encoding each line of the information, thus reducing the size thereof and band-decoding the same to restore it to the original size, and a pattern generator 40 storing pattern information representing characters, symbols, etc. The main control unit 10 further comprises a display interface 42 for supplying the CRT display unit 18 with data and control signals which are necessary to operate the CRT display unit 18.

The main memory 32 and keyboard 16 are connected to CPU 30 by a control bus CB. The units 12, 14, 18 and 20, the memory 34, buffer 36, circuit 38, pattern generator 40 and display interface 42 are connected to CPU 30 by a data bus DB.

Figure 4:
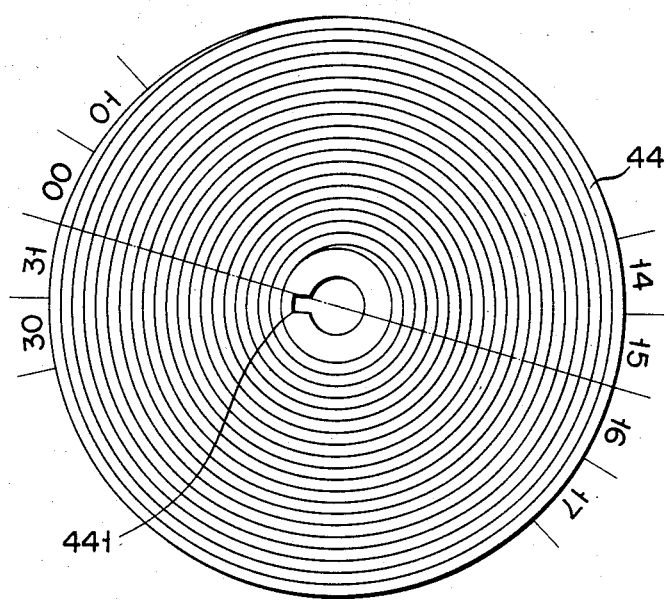
FIG. 4 is a schematical plan view of an optical disk used in the system of FIG. 1.

The display interface 42 and CRT display unit 18 form an image information display device. The optical disk 44, i.e., a first storage, consists of a circular substrate made of glass or plastics and a doughnut-shaped metal film of tellurium or bismuth coated on the substrate. As shown in FIG. 4, a notch or reference position mark $44_1$ is cut in the central portion of the metal film. The disk 44 consists of 32 sectors, 00 to 31, sequentially arranged in the circumferential direction of the disk 44, the first sector 00 and the last sector 31 being separated by a line extending from the center of the disk 44 and passing the mark $44_1$. A spiral groove is cut in the metal film. Serial track numbers are assigned to the turns of the spiral groove, the first number to the innermost turn and the last number to the outermost turn.

Figure 5:
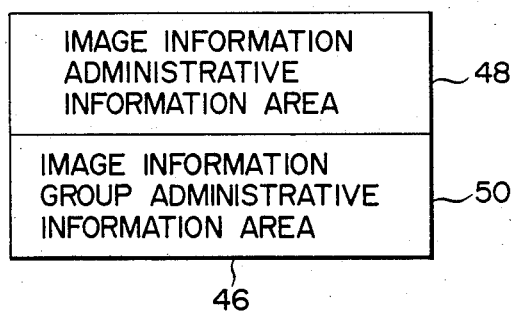
FIG. 5 shows the storage areas of a floppy disk used in the system of FIG. 1.

As shown in FIG. 5, two storage areas 48, 50 of the floppy disk 46 are used to store two types of information, respectively. One type is information for administrating image information, and the other type is information for administrating an image information group. (These areas 48, 50 will be hereinafter referred to as "retrieval data area" and "identification data area").

As shown in FIG. 6, the retrieval data area 48 consists of a 2-byte storage area NI, a 2-byte storage area NTADR, a 1-byte storage area NSADR and a 20-byte storage area RD. The area NI is used to store the serial number of any image information stored in the optical disk 44. The areas NTADR, NSADR are used to store the track number and sector number of the next image information, respectively. The area RD is used to store the retrieval data corresponding to the image information. The retrieval data includes a 16-byte retrieval code and a 4-byte address data. The retrieval code consists of at most six items. For example, it may be formed of a 1-byte data designating patent or utility model, a 1-byte data designating the Christian year or Japanese year, a 2-byte data representing the year of issuance of a patent or registration of a utility model, an 8-byte data showing the serial number of the patent or utility model, and a 4-byte data representing the number of pages of the patent of utility model specification. The address data may be formed of a 1-byte data L representing the amount of the image information (e.g., the number of sectors), a 2-byte track address data TADR of the track on which the image information is stored, and a 1-byte sector address data SADR of the sector in which the image information is stored.

Figure 7:
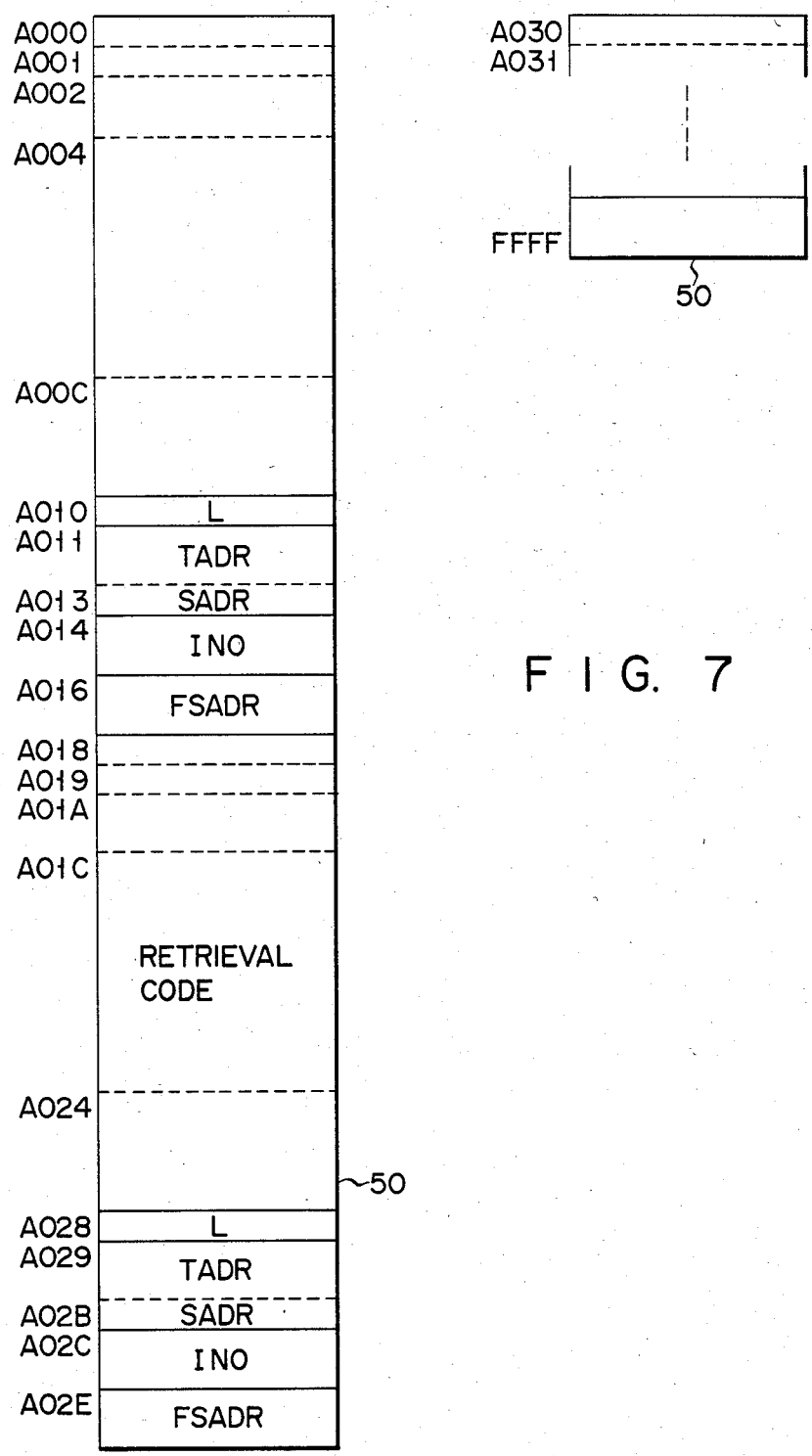
FIG. 7 shows how items of other information for administrating image information groups are stored in another storage area of the floppy disk.

As illustrated in FIG. 7, the identification data area 50 consists of an image information group number storage area INO, address storage areas TADR, SADR, and an address storage area FSADR. The area INO is used to store the serial number of an image information group. The areas TADR, SADR are used to store the title of the image information group (e.g., the number of a patent specification), a table-of-contents data, the titles of the items of this data. The area FSADR is used to store the data designating the starting address of the 20-byte storage area RD of the retrieval data area 48.

The operation of the document filing system shown in FIGS. 1, 2 will now be described with reference to the flow charts shown in FIGS. 8A-1 to 8D.

When a power supply switch (not shown) is closed, CPU 30 makes the floppy disk unit 22 read data from the storage areas 48, 50 of the floppy disk 46 and then stores this data in the title memory 34. This is step S1. In step S2, the operator selects the registration mode by operating the keyboard 16. In step S3, he operates the keyboard 16, thus inputting the retrieval code of the image information to be registered.

In step S4, CPU 30 performs various operations to register this retrieval code in the RAM of the main memory 32. More specifically, the retrieval code is checked so as to ascertain whether or not its format is identical with predetermined format, in respect of the number of items to be stored in each storage sub-area of the area RD, the kind of characters to be stored in the storage sub-area, etc. Suppose the format of the retrieval code is identical with the predetermined one. Then, in step S5, the code is compared with the retrieval data already stored in the title memory 34, thereby to determine whether or not the same code has been stored in the RAM of the main memory 32. In step S6, the retrieval code is stored in the RAM if the same code has not been stored therein.

In step S7, CPU 30 causes the CRT display unit 18 to display the message, "PLEASE INPUT IMAGE INFORMATION". Therefore, the operator sets the original 24 to the two-dimensional scanning unit 12 in step S8. In step S9, CPU 30 makes the optical disk unit 14 and two-dimensional scanning unit 12 start performing their functions.

In step S10, the two-dimensional scanning unit 12 scans the original 24 and converts the image information printed on the original 24 into electric signals. The image information, i.e., the electric signals, is stored in the page buffer 36, line by line. When all one-page image information is stored in the buffer 36, it is transferred to the display interface 42.

In step S11, the one-page information is displayed by the CRT display unit 18. Suppose this information is correct. Then, in step S12, the operator pushes a registration key (not shown) of the keyboard 16. CPU 30 outputs a control signal to the page buffer 36. In response to this signal the buffer 36 transfers the one-page image information to the encoding/decoding circuit 38, line by line. In step S13, the circuit 38 performs the modified Hoffman (MH) transform, thus band-encoding each line of the one-page information and supplies the information thus band-encoded, to the optical disk unit 14. In step S14, CPU 30 reads the track number and starting sector number from the storage areas NTADR and NSADR of the title memory 34 and supplies these numbers to the optical disk unit 14. In step S15, the unit 14 stores the one-page image information in the track designated by the track number and extending in the sector designated by the sector number and also extending in the following sectors of the optical disk 44.

When the one-page image information is stored in the disk 44, CPU 30 stores the track number, starting sector number, and data showing the amount of image data stored in the disk 44, etc. in the RAM of the main memory 32 in accordance with the format of the retrieval code stored in the RAM. As a result, in step S16, an address is formed and stored in the RAM. In step S17, retrieval data is formed and stored in the title memory 34 and also in the retrieval data area 48 of the floppy disk 46. In step S18, CPU 30 increments the contents of the storage areas NI of the memory 34 and disk 46 by 1 and then renews the contents of the storage areas NTADR, NSADR in accordance with the amount of the image information stored in the optical disk 44.

Any other one-page image information is processed and stored in the optical disk 44 in the same manner as described above.

To register the table of contents concerning groups of image information items before these groups are stored in the optical disk 44, the titles and serial numbers of these groups are input as retrieval codes by operating the keyboard 16 and a key, e.g., the "!" key, which is used to designate a table of contents. This is done in step S3'. In step S19, CPU 30 stores the retrieval code in the RAM of the main memory 32. Further, in step S20, CPU 30 causes the CRT display unit 18 to display the message, "PLEASE INPUT TABLE OF CONTENTS". When this message is displayed, the operator sets the page or pages of the table of contents to the two-dimensional scanning unit 12, in step S21. In step S22, CPU 30 makes the optical disk unit 14 and scanning unit 12 perform their respective functions.

The two-dimensional scanning unit 12 scans the pages of the table of contents and converts the information printed on these pages into electric signals. The image information, i.e., the signals, is stored in the page buffer 36, line by line, in step S23. When one page of information is stored in the buffer 36, it is immediately transferred to the display interface 42. In step S24, the one-page image information is displayed by the CRT display unit 18.

Suppose the one-page information displayed by the CRT display unit 18 is found to be correct. Then, in step S25, the operator depresses the registration key (not shown). CPU 30 then supplies a control signal to the page buffer 36. In response to this signal, the buffer 36 transfers the one-page image information to the encoding/decoding circuit 38, line by line. In step S26, the circuit 38 performs the modified Hoffman (MH) transform, thus band-encoding each line of the one-page information and supplies the one-page information, thus band-encoded, to the optical disk unit 14. In step S27, CPU 30 reads the renewed track number and renewed starting sector number from the storage areas NTADR, STADR of the title memory 34 and supplies these numbers to the optical disk unit 14. In step S28, the one-page information, i.e., the first page of the table of contents, is stored in the track designated by the renewed track number and extending in the sector designated by the starting sector number and also extending in the following sectors of the optical disk 44.

When the one-page image information, i.e., the first page of the table of contents, is stored in the optical disk 44, CPU 30 forms an address consisting of the track number, starting sector number and data showing the amount of the image information stored in the disk 44, etc. and stores this address and the starting address of the title memory 34 in the RAM of the main memory 32 in accordance with the format of the retrieval code already stored in the RAM. This is done in step S29. As a result, identification data is formed, which consists of various items, i.e., the title of the image information group, the serial number of the group, the track number, the starting sector number, the amount of image information stored, and the starting address of the retrieval data area 48. CPU 30 then stores this identification data in the title memory 34 and supplies it to the floppy disk unit 22. Hence, the identification data is stored in the identification data area 50 of the floppy disk 46. Storing the identification data in the memory 34 and floppy disk 46 is carried out in step S30. In step S30', CPU renews the contents of the storage areas NTADR, NSADR of the title memory 34 and floppy disk 46.

The other pages of the table of contents and the table of contents concerning any other group of image information items are stored in the optical disk 44 in the same manner as described above.

Figures 1, 8C:
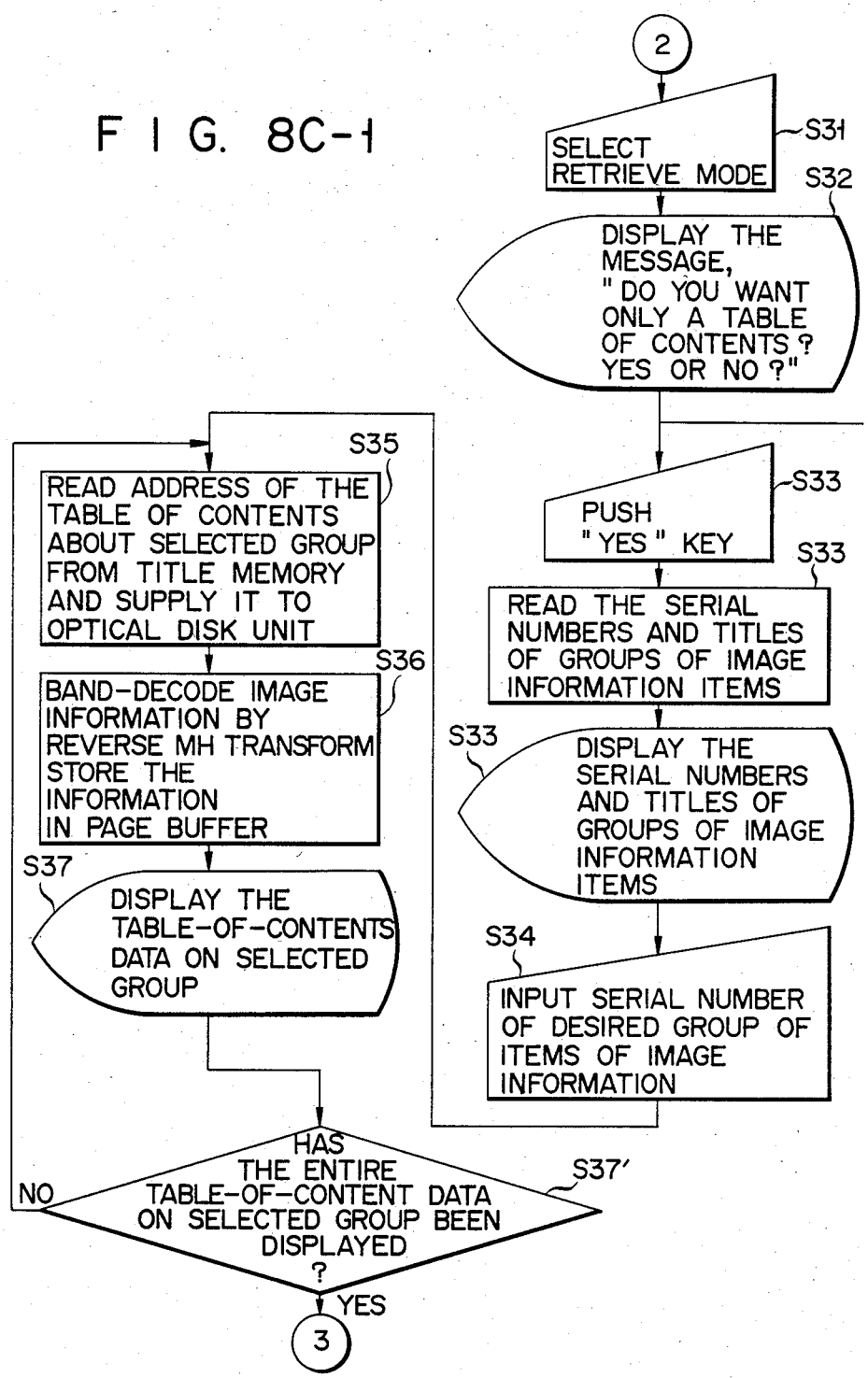
Figures 2, 8C:
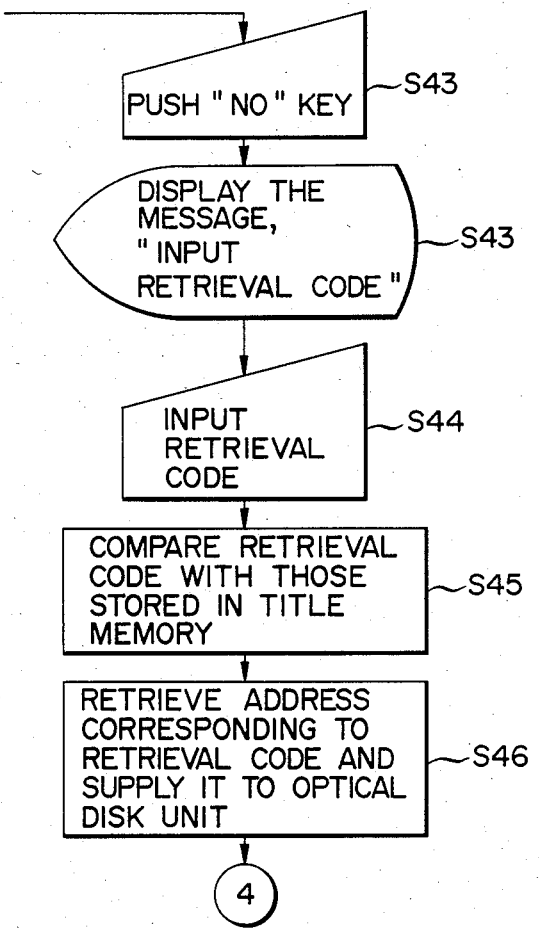
FIG. 2 is a perspective view of the document filing system shown in FIG. 1.

It will now be described how the image information is retrieved from the optical disk 44, with reference to the flow charts of FIGS. 8C-1 and 8C-2.

In step S31, the operator selects the retrieve mode by operating the keyboard 16. In step S32, CPU 30 causes the CRT display unit 18 to display the message, "DO YOU WANT ONLY A TABLE OF CONTENTS? PLEASE DEPRESS YES OR NO KEY". Suppose the operator wishes to obtain the table of contents only. Then, in step S33, he pushes a "YES" key provided on the CRT display unit 18, and CPU 30 reads the serial numbers and titles of the groups of image information items and makes the CRT display unit 18 display the serial numbers and titles. In step S34, the operator inputs the serial number of the group which he wishes to obtain, by operating the keyboard 16. CPU 30 reads the address of the page of the table of contents (i.e., the track number and starting sector number), on which the desired group of information items are listed, from the identification data area 50 of the title memory 34. CPU 30 then instructs the optical disk unit 14 to reproduce the page of the table of contents. This operation is accomplished in step S35.

The optical disk unit 14 supplies the encoded one-page image information to the encoding/decoding circuit 38, line by line. In step S36, the circuit 38 performs the reverse MH transform on each line of the one-page information, thus band-decoding the information and supplying the same back to the page buffer 36, line by line. When the one-page information is stored in the buffer 36, CPU 30 causes the CRT display unit 18 to display the one-page image information (i.e., the one-page of the table of contents) in step S37. This one-page information includes the title and serial number of the desired group, the chapter numbers, and titles and page numbers of the items of the group.

If the operator inputs the serial numbers of two or more groups, e.g., "3 to 30", in step S34, steps S35 to S37 are repeated 28 times, thereby to display the pages of the table of contents, on which the groups 3 to 30 are listed. As a result, these pages are displayed, one after another at a predetermined speed. Hence, the operator can read these pages as if he were skimming table-of-contents pages of a book.

In step S38, the operator reads the one-page image information displayed by the CRT display unit 18 and operates the keyboard 16, thus inputting the page number of the item of image information which he wishes to obtain. Then, CPU 30 reads the starting address of the retrieval data area 48 of the title memory 34. In step S39, in accordance with the starting address thus read and the page input by the operator, CPU 30 reads the track number and starting sector number of the item of image information from the title memory 34. In step S40, CPU 30 instructs the optical disk unit 14 to reproduce the table-of contents data.

In step S41, the optical disk 14 supplies the encoded image information to the encoding/decoding circuit 38, line by line, and the circuit 38 band-decodes this encoded information, thus restoring the image information, which is supplied to the page buffer 36, line by line. When one page of this image information is stored in the buffer 36, it is supplied through the display interface 42 and displayed by the CRT display unit 18, thus providing a soft copy, or printed by the recording unit 20, thus providing a hard copy, in step S42.

Suppose the operator pushes a "NO" key provided on the CRT display unit 18 in step 75'. Then, in step S43, CPU 30 causes the CRT display unit 18 to display the message, "PLEASE INPUT RETRIEVAL CODE". In step S44, the operator inputs the retrieval code of the item of information which he wants to obtain, by operating the keyboard 16. In step S45, CPU 30 compares the retrival code with the retrieval codes stored in the retrieval data area 48 of the title memory 34, one after another. If the same retrieval code is stored in the data area 48, CPU 30 retrieves the track number and starting sector number which correspond to this retrieval code and instructs the optical display unit 14 to read the image information corresponding to the address of the retrieval code. This is done in step S46.

Thereafter, steps S41 and S42 are repeated, whereby the image information corresponding to the retrieval code input by the operator is displayed on the CRT display unit 18, thus providing a soft copy, or printed by the recording unit 20, thus providing a hard copy. The other items of image information may be retrieved in the same manner as described above.

As described above, with the document filing system shown in FIGS. 1 and 2, the operator can easily and quickly judge whether or not a group of items of image information are the very items that he wishes to obtain and can retrieve the items of image information without operating the keyboard many times.

The present invention is not limited to the embodiment described above. For example, the summary of each item of image information may be displayed instead of the table-of-content data of a group of image information, i.e., the chapter numbers, titles and page numbers of the items of image information. A second embodiment which can display the summaries of the items of image information will now be described.

The document filing system according this second embodiment is substantially the same in structure as the system of FIGS. 1 and 2. It also uses the optical disk as shown in FIG. 4. Hence, the components of this system will be designated by the same numerals as used in FIGS. 1, 2, 3 and 4 and will now be described in detail.

The second embodiment of the invention uses a floppy disk 61 as a second storage. As shown in FIG. 9, two adjacent storage areas 62, 63 of the disk 61 are used to store the retrieval data and summary data of an item of image information, respectively. (These areas 62, 63 will be hereinafter referred to as "retrieval data area" and "summary data area".)

Figure 10:
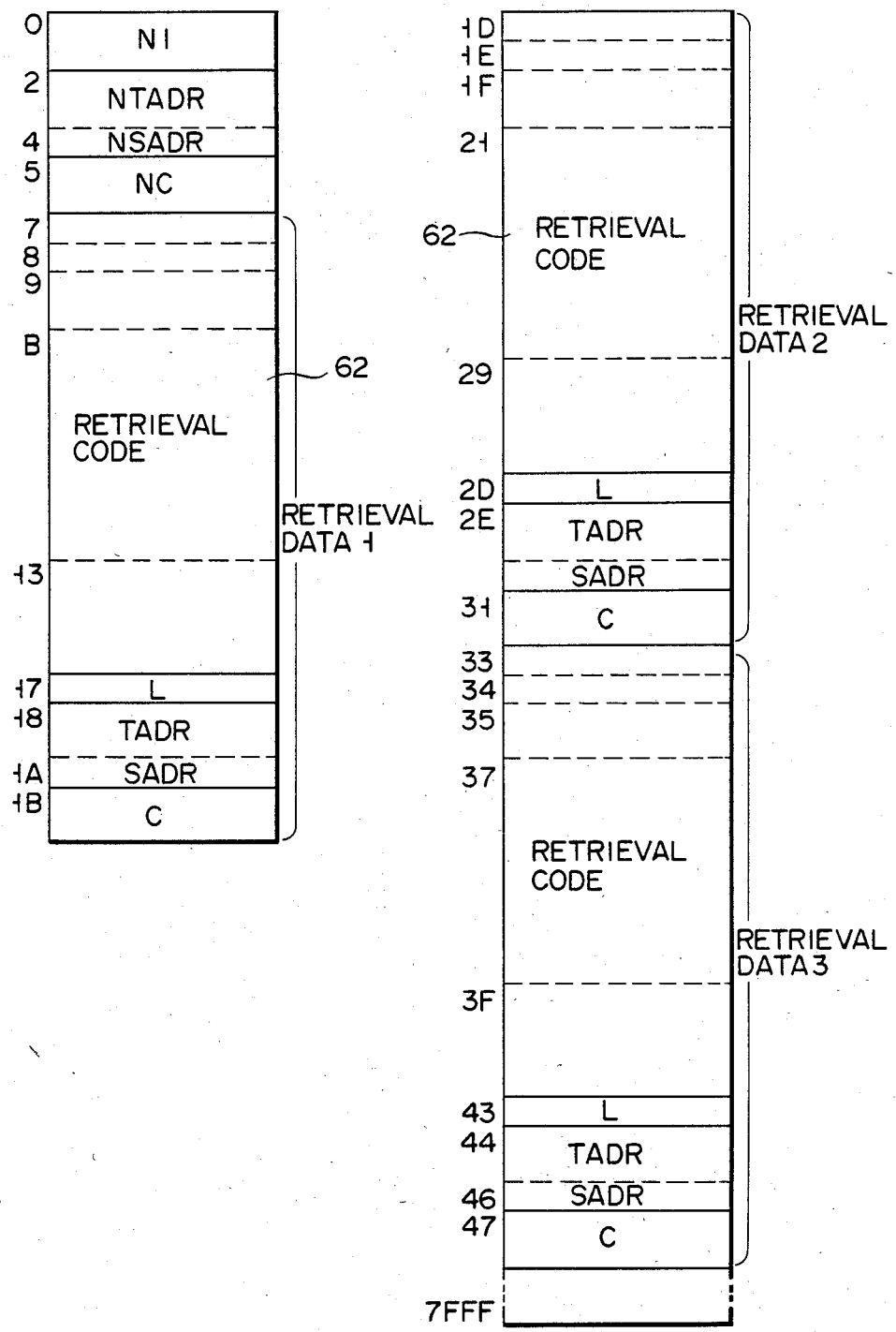
FIG. 10 illustrates how items of retrieval data are stored in the retrieval data area of the floppy disk shown in FIG. 9.

As shown in FIG. 10, the retrieval data area 62 consists of a 2-byte storage area NI, a 2-byte storage area NTADR, a 1-byte storage area NSADR, a 2-byte storage area NC, and a 22-byte storage area RD. The area NI is used to store the serial number of any image information. The area NTADR is used to store the track number of the next image information. The area NSADR is used to store the sector number of the next image information. The area NC is used to store the serial number of the summary of the next image information. The area RD is to store the retrieval data of the image information. The retrieval data includes a 16-byte retrieval code, a 4-byte address data and a 2-byte data representing the serial number of the summary of the image information. The retrieval code consists of at most six items. For example, it may be formed of a 1-byte data designating patent or utility model, a 1-byte data designating the Christian year or Japanese year, a 2-byte data representing the year of issuance of a patent or registration of a utility model, an 8-byte data showing the serial number of the patent or utility model, and a 4-byte data representing the number of pages of the patent or utility model specification. The address data may be formed of a 1-byte data L representing the amount of the image information (e.g., the number of sectors), a 2-byte track address data TADR and a 1-byte sector address data SADR.

Figure 11:
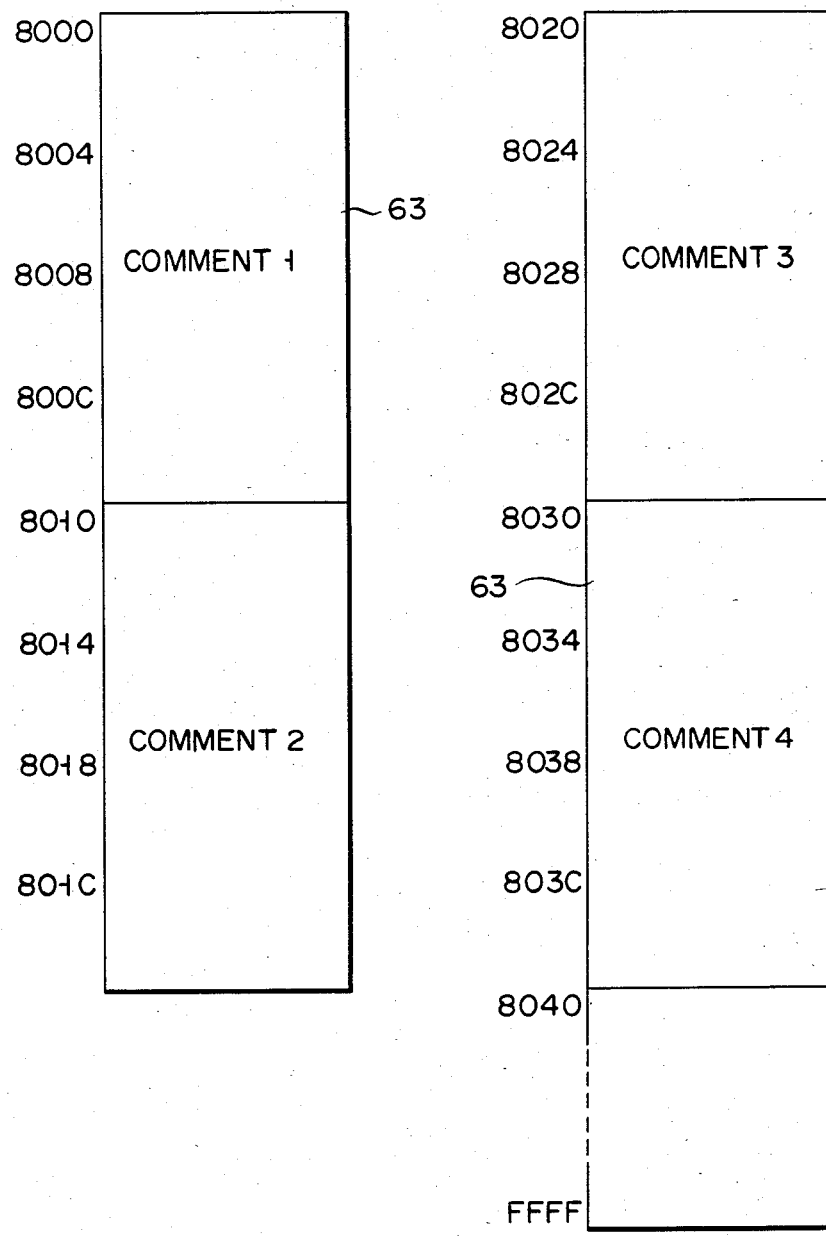
FIG. 11 schematically illustrates how items of summary data are stored in the summary data area of the floppy disk shown in FIG. 9.

As shown in FIG. 11, the summary data area 63 stores 16-byte items of summary data.

Figures 1, 12A:
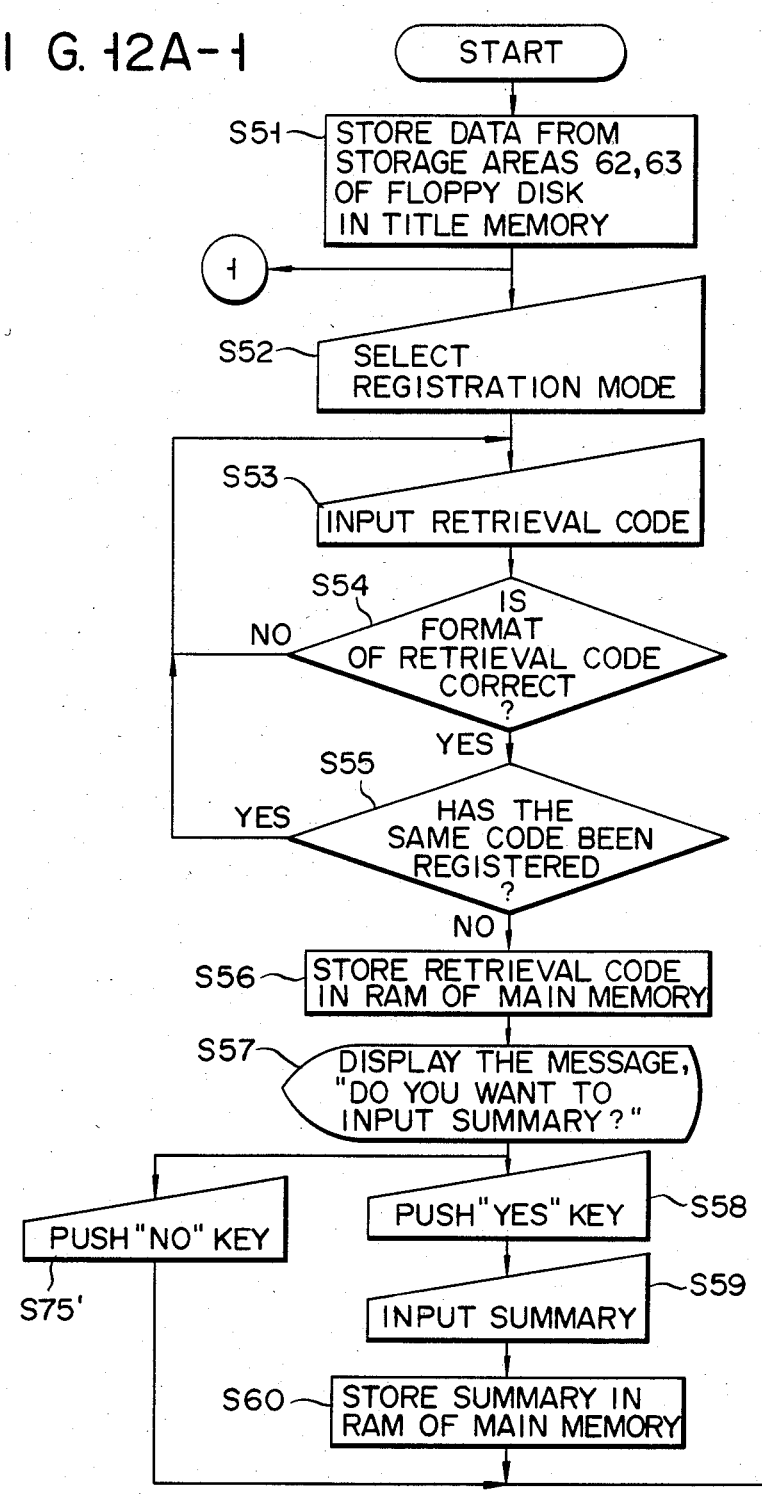
Figures 2, 12A:
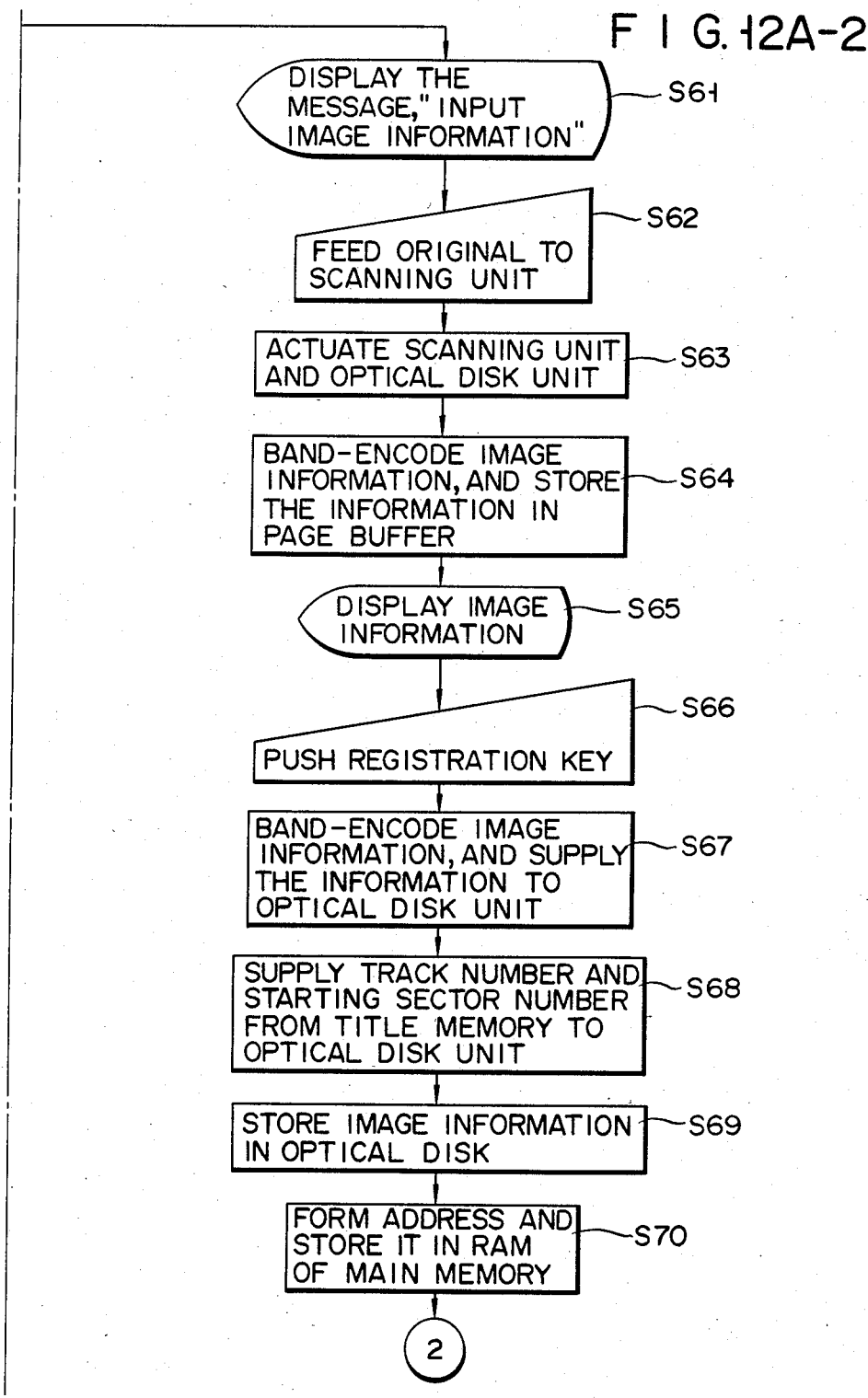
Figure 12B:
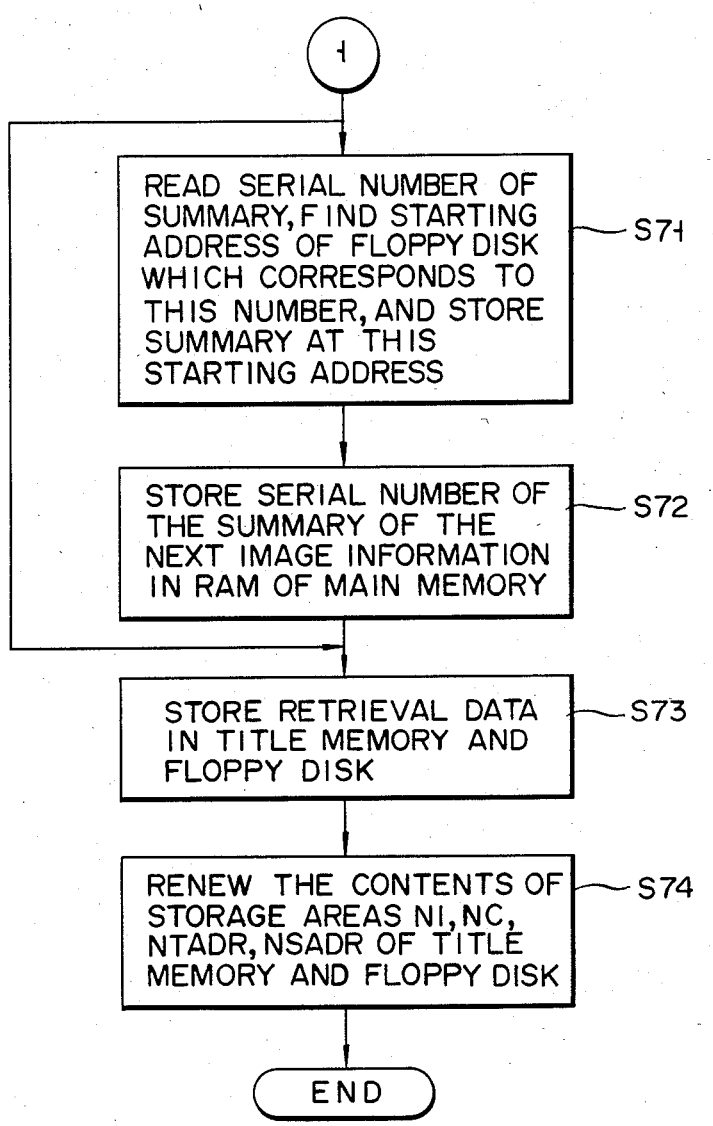
Figure 12D:
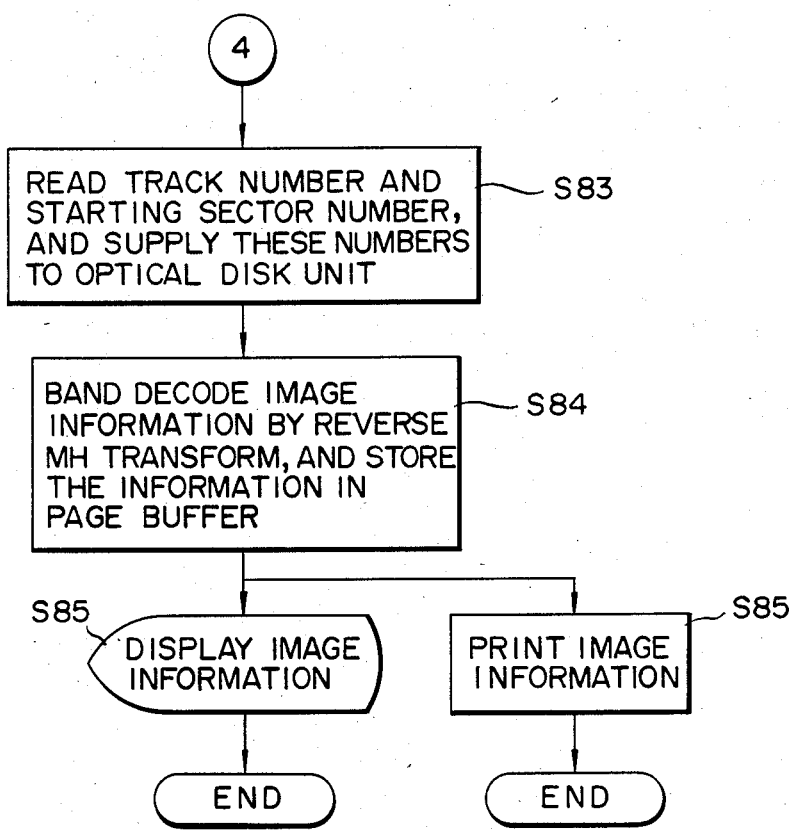
Figure 12E:
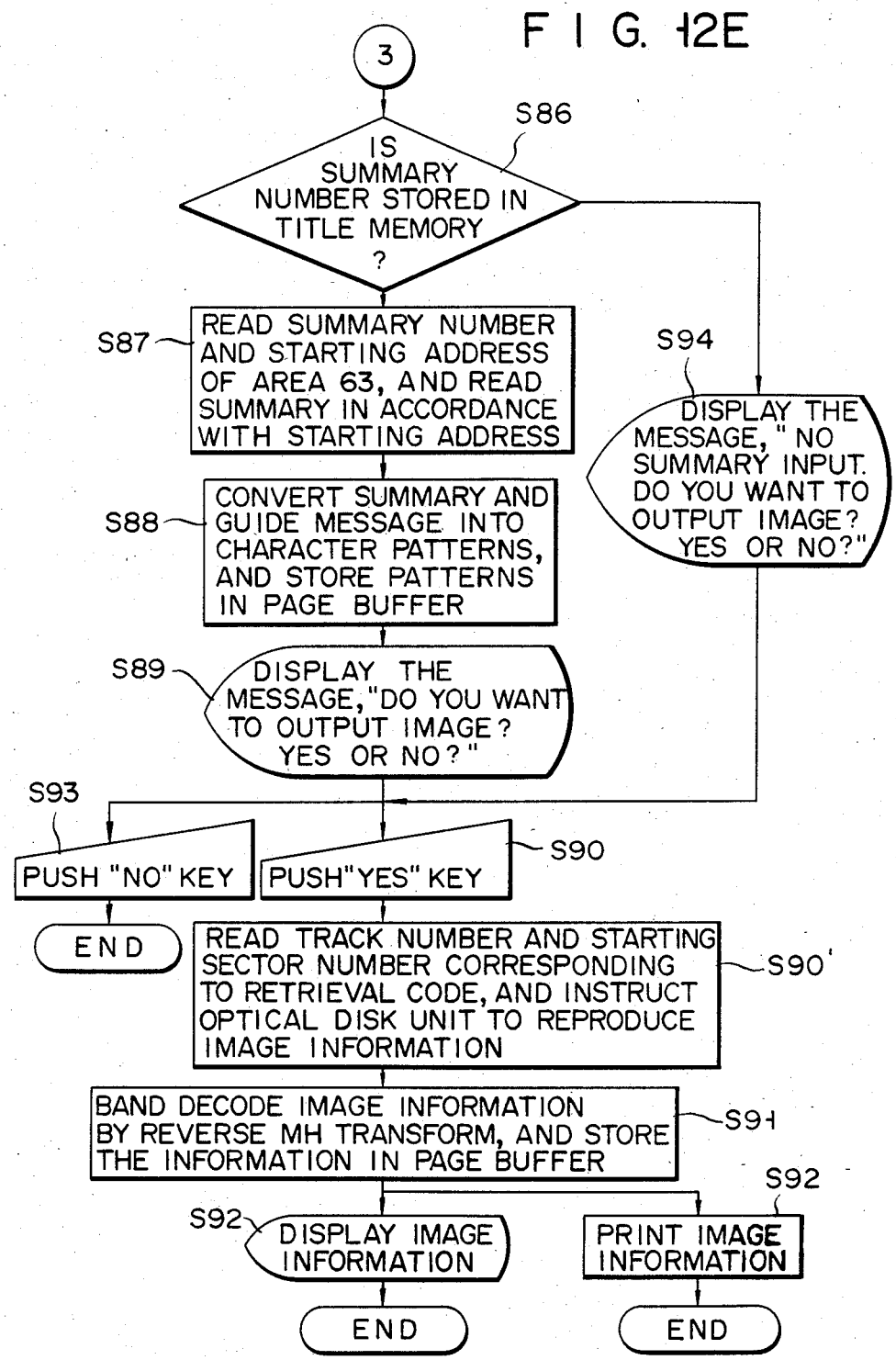

The operation of the document filing system according to the second embodiment will now be described with reference to the flow charts of FIGS. 12A-1 to 12E.

First, a power supply switch (not shown) is closed. Then, in step S51, CPU 30 makes the floppy disk unit 22 read data from the storage areas 62, 63 of the floppy disk 61 and then stores this data in the title memory 34. In step S52, the operator selects the registration mode by operating the keyboard 16. In step S53, he operates the keyboard 16, thus inputting the retrieval code of the image information which he wishes to register.

In step S54, CPU 30 checks the retrieval code so as to ascertain whether or not the format of the code is identical with a predetermined format, in respect of the number of items to be stored in each storage sub-area of the area RD, the kind of characters to be stored in the storage sub-area, etc. Suppose the format of the retrieval code is identical with the predetermined one. Then, in step S55, CPU 30 compares the code with the retrieval data already stored in the title memory 34, to thereby determine whether or not the same code has been stored in the RAM of the main memory 32. In step S56, the retrieval code is stored in the RAM if the same code has not been stored therein.

In step S57, CPU 30 causes the CRT display unit 18 to display the message, "DO YOU WANT TO INPUT SUMMARY? PLEASE PRESS YES OR NO KEY". Suppose the operator wishes to input summary. The operator pushes a "YES" key in step S58. In step S59, he operates the keyboard 16, thereby inputting the summary. In step S60, CPU 30 stores the summary data in the RAM of the main memory 32. In step S61, CPU 30 makes the CRT display unit 18 display the message, "PLEASE INPUT IMAGE INFORMATION". Therefore, the operator sets an original 24 to the two-dimensional scanning unit 12, in step S62. In step S63, CPU 30 instructs the scanning unit 12 and optical disk unit 14 to start performing their functions.

The two-dimensional scanning unit 12 scans the original 24 and converts the image information printed on it into electric signals, and the image information, i.e., these signals, is stored in the page buffer 36, line by line. When all one-page image information is stored in the buffer 36, it is transferred to the display interface 42. This is done in step S64. In step S65, this one-page image information is displayed by the CRT display unit 18.

Suppose the one-page image information displayed by the CRT display unit 18 is correct. Then, in step S66, the operator pushes the registration key (not shown). CPU 30 outputs a control signal to the page buffer 36. In response to this signal the buffer 36 transfers the one-page image information to the encoding/decoding circuit 38, line by line. In step S67, the circuit 38 performs the modified MH transform, thus band-encoding each line of the image information and supplies the information, thus band-encoded, to the optical disk unit 14. In step S68, CPU 30 reads the track number and starting sector number from the storage areas NTADR, NSADR of the title memory 34 and supplies these numbers to the optical disk unit 14. In step S69, the unit 14 stores the one-page image information in the track designated by the track number and extending in the sector designated by the sector number and also extending in the following sectors of the optical disk 44.

When the one-page image information is stored in the disk 44, CPU 30 stores the track number, starting sector number, and data showing the amount of image information, etc. in the RAM of the main memory 32, thereby forming an address, and stores this address in the RAM of the main memory 32 in addition to the retrieval code. This is done in step S70. If the summary of the image information is stored in the optical disk 44, CPU 30 reads the serial number of this summary from the retrieval data area 62 of the floppy disk 61, finds the starting address of the summary data area 63 which corresponds to the serial number, and store the summary at this address. This is carried out in step S71. In step S72, CPU 30 stores the serial number of the summary of the next image information, i.e., the summary number C, in the RAM of the main memory 32 in addition to the retrieval code. As a result, retrieval data is formed in the RAM of the main memory 32. This retrieval data consists of the retrieval code, track number, starting sector number, the amount of image information, and the serial number of summary, etc.

CPU 30 supplies this retrieval data to the title memory 34 and floppy disk unit 22. Therefore, the retrieval data is stored in the retrieval data areas 62 of the title memory 34 and floppy disk 61 in step S73. In step S74, CPU 30 increments by 1 the contents of the storage areas NI and NC of the memory 34 and disk 61 and renews the data in the storage areas NTADR, NSADR in accordance with the amount of the image information.

If the operator pushes a "NO" key in step S75 in response to the message displayed in step S57, steps S61 to S74 will be repeated. In this case, however, no serial number of summary is stored, the data in the storage area NC is not renewed, and no summary is stored in the summary data area 63.

Other items of image information may be processed and stored in the disk 44 in the same way as described above, whether or not summaries of these items are available.

How the image information is retrieved from the disk 44 will now be described with reference to FIGS. 12C to 12E.

FIrst, the operator selects the retrieve mode in step S75. In step S76, CPU 30 makes the CRT display unit 18 display the message, "PLEASE INPUT RETRIEVAL CODE". In step S77, he inputs the retrieval code of the image information, by operating the keyboard 16. In step S78, CPU 30 compares the code with the retrieval codes stored in the retrieval data area 62 of the title memory 34. In step S79, it is ascertained whether or not two or more identical codes are stored in the memory 34. Suppose two or more identical codes are stored in the memory 34. Then, in step S79, CPU 30 reads the summary numbers corresponding to these identical retrieval codes, the starting addresses of the area 63 which correspond to the summary numbers, and the summaries designated by these summary numbers. The summaries and identical retrieval codes are converted into character patterns by the pattern generator 40, which are stored in the page buffer 36, in step S80. In step S81, CPU 30 supplies the identical codes and the summaries through the display interface 42, thus displaying the codes and summaries. In step S82, the operator inputs the serial number of the retrieval code and pushes an "IMAGE OUTPUT" key (not shown). In step S83, CPU 30 reads the track number and starting sector number which correspond to the retrieval code and instructs the optical disk unit 14 to reproduce the image information stored in the optical disk 44 at the address corresponding to the track number and sector number.

The optical disk unit 14 supplies the encoded image information to the encoding/decoding circuit 38, line by line. In step S84, the circuit 38 performs the reverse MH transform on each line of the image information, thus, band-decoding the information and supplying the same back to the page buffer 36. When one page of the image information is stored in the buffer 36, CPU 30 causes the CRT display unit 18 to display the one-page information in step S85, using the display interface 42. Alternatively, in step S85, CPU 30 may cause the recording unit 20 to print the one-page image information.

Suppose only one retrieval code which is identical with the code input by the operator is found in the title memory, in step S79. Then, in step S86, CPU 30 ascertains whether or not the summary number corresponding to this identical retrieval code is stored in the retrieval data area 62 of the title memory 34. If this summary number is stored in the area 62, CPU 30 reads the summary number, the starting address of the summary data area 63 in accordance with the summary number, and reads the summary from the title memory 34 in accordance with the starting address. This is carried out in step S87. In step S88, this summary and the messages teaching the operator how to read the summary are converted by the pattern generator 40 into character patterns, which are stored in the page buffer 36. In step S89, CPU 30 makes the CRT display unit 18 display the message, "DO YOU WANT TO OUTPUT IMAGE? PLEASE PUSH YES OR NO KEY", using the display interface 42. Suppose the operator pushes the "YES" key in step S90. In step S90', CPU 30 reads the track number and starting sector number corresponding to the retrieval code and instructs the optical disk unit 14 to reproduce the image information stored in the disk 44 at the address corresponding to the track number and sector number.

In step S91, the optical disk unit 14 supplies the encoded image information to the encoding/decoding circuit 38, line by line, and the circuit 38 band-decodes this image information, thus restoring the image information, which is supplied to the page buffer 36, line by line. When one page of this information is stored in the buffer 36, it is supplied through the display interface 42 and displayed by the CRT display unit 18, thus providing a soft copy, or printed by the recording unit 20, thus providing a hard copy. This is carried out in step S92. If the "NO" key is pushed in step S89, the operation is stopped in step S93.

Suppose no summary corresponding to the sole retrieval code identical with the code input by the operator is found in the retrieval data area 62, in step S86, CPU 30 makes the CRT display unit 18 display the message, "NO SUMMARY INPUT. DO YOU WANT TO OUTPUT IMAGE? PLEASE DEPRESS YES OR NO KEY" in step S94. Thereafter, steps S90 to S93 are repeated.

As described above, with the document filing system according to the second embodiment, the operator can easily and quickly judge whether or not each item of image information is the very item that he wishes to obtain and can retrieve the item without operating the keyboard many times.

In the embodiments described above, the identification data or the summary data is stored in a floppy disk. The data may be stored in an optical disk, instead of a floppy disk.

In the first embodiment described above, the table-of-contents data, i.e., the chapter numbers, titles of items of image information, are input by the two-dimensional scanning unit. Instead, the table-of-contents data may be input by operating the keyboard. In the second embodiment described above, summaries of items of image information are input by operating the keyboard. Instead the summaries may be input by the two-dimensional scanning unit.

What is claimed is:

1. A document filing system comprising:
   input means for selectively inputting a plurality of items of image information, retrieval data and title data, and for selectively inputting a code corresponding to the title data corresponding to desired image information;
   first storing means for storing a plurality of items of image information input by the input means at a corresponding plurality of addresses;
   processing means including: first read/write means for selectively writing the items of image information in, and for selectively reading the items of image information from, the first storing means; and addressing means for applying to said first read/write means an address of said first storing means corresponding to a code input by said inputting means in order to read out desired image information from said first storing means;
   second storing means including a retrieval data area for storing retrieval data of each item of image information inputted by the input means and a title data area for storing title data corresponding to each of plural item groups of image information into which image items are classified and which represent respective titles;
   second read/write means for selectively writing retrieval data in, and selectively reading the retrieval data from, the retrieval data area of the second storing means and for writing title data in and reading the title data from the title data area of the second storing means;
   means for retrieving the image information in accordance with the retrieval data input by said input means; and
   output means for outputting the title data of each item group in the form of a soft copy or a hard copy, said output means obtaining said title data from the title data area of said second storing means to select the title data corresponding to desired image information from displayed or printed title data.

2. A document filing system according to claim 1, wherein said input means includes a keyboard.

3. A document filing system according to claim 1, wherein said input means includes a two-dimensional scanning device for scanning a document so as to produce image information.

4. A document filing system according to claim 1, wherein said input means can designate a plurality of items of title data and said output means includes a display device which displays items of title data at predetermined intervals.

5. A document filing system according to claim 1, wherein said output means includes a display device which displays the retrieval data, title data and image information.

6. A document filing system according to claim 1, wherein said output means includes a hard-copying device which outputs at least the image information in the form of a hard copy.

7. A document filing system according to claim 1, wherein said first storing means includes an optical disk and said first read/write means includes an optical disk device.

8. A document filing system according to claim 1, wherein said second storing means includes a floppy disk and said second read/write means includes a floppy disk device.

9. A document filing system according to claim 1, wherein said output means includes a CRT display device.

10. A document filing system comprising:
    input means for inputting image information, retrieval data and corresponding summary data representing a summary of the inputted image information.
    first storing means for storing a plurality of items of image information input by the input means;
    processing means including first read/write means for writing image information in, and reading the image information from, the first storing means;
    second storing means including a retrieval data area for storing retrieval data of each item of information and a summary data area for storing the corresponding summary data;
    second read/write means for writing retrieval data in, and reading the retrieval data from, the retrieval data area of the second storing means and for writing summary data in, and reading the summary data from, the summary data area of the second storing means;
    said processing means further including means for retrieving the image information in accordance with the retrieval data input by said input means; and output means for outputting the summary data of each image information read from the summary data area of said second storing means in the form of a soft copy or a hard copy, for retrieval.

11. A document filing system according to claim 10, wherein said input means includes a keyboard.

12. A document filing system according to claim 10, wherein said input means includes a two-dimensional scanning device for scanning a document so as to produce image information.

13. A document filing system according to claim 10, wherein said output means includes a display device which displays the retrieval data, summary data and image information.

14. A document filing system according to claim 10, wherein said output means includes a hard-copying device which outputs at least the image information in the form of a hard copy.

15. A document filing system according to claim 10, wherein said first storing means includes an optical disk and said first read/write means includes an optical disk device.

16. A document filing system according to claim 10, wherein said second storing means includes a floppy disk and said second read/write means includes a floppy disk device.

17. A document filing system according to claim 10, wherein said output means includes a CRT display device.

18. A method of filing information including the steps of:
(1) inputting a block of information corresponding to at least one image;
(2) inputting a retrieval code to be associated with said inputted block of information;
(3) inputting descriptive information including a summary of the content of said image;
(4) storing said block of information in a first memory device at a selected address;
(5) storing an index record including said retrieval code, descriptive information and selected address in a second memory device;
(6) inputting a retrieval code associated with a record to be retrieved;
(7) searching for and locating an index record stored in said second memory device including a retrieval code stored by said storing step (5) which matches the retrieval code inputted by said inputting step (6);
(8) displaying the descriptive information included on the index record located by said searching step (7);
(9) reading the block of information stored at the address of said first memory device equal to the address included in said index record located by said searching step (7), and
(10) displaying the image represented by the block of information read by said reading step (9).

19. A method as in claim 18 further including, subsequent to said displaying step (8) and prior to said reading step (9), the steps of:
(a) querying whether display of the image the content of which is summarized by said summary displayed by said displaying step (8) is desired;
(b) inputting an affirmative response if the display of said image is desired in response to said querying step (a); and
(c) selectively performing said reading step (9) and said displaying step (10) in response to the input of an affirmative response by said inputting step (b).

20. A system for filing information including:
first inputting means for selectively inputting retrieval codes, query responses and/or descriptive information;
second inputting means for inputting blocks of image information each representing at least one image;
first mamory means for storing index records;
second memory means for storing said blocks of image information inputted by said second inputting means;
processing means including first read/write means for selectively working information into and reading information from said first memory means;
second read/write means for writing blocks of information into and reading blocks of information from said second memory means;
displaying means for displaying information; and
said processing means, operatively coupled to said first and second inputting means, second read/write means, and said displaying means, for:
(1) cooperating with said second inputting means to input a block of image information corresponding to at least one image,
(2) cooperating with said first inputting means to input a retrieval code associated with said block of image information and to input corresponding descriptive information including a summary of the content of said image,
(3) cooperating with said second read/write means to store said block of image information inputted by said second inputting means in said second memory means at a selected address,
(4) cooperating with said first read/write means to store an index record including said retrieval code and corresponding descriptive information inputted by said first inputting means and said selected address in said first memory means,
(5) cooperating with said first inputting means to input a retrieval code associated with a block of image information to be retrieved,
(6) cooperating with said first read/write means to search for and locate an index record stored in said first memory means which includes a retrieval code matching the retrieval code associated with a record to be retrieved inputted by said first inputting means,
(7) cooperating with said displaying means to display the descriptive information included in the located index record,
(8) cooperating with said second read/write means to read the block of information stored at the address of said second memory means equal to the address included in said located index record, and
(9) cooperating with said displaying means to effect display of the image represented by said block of image information read from said second memory means.

21. A system as in claim 20 wherein said processing means also:
cooperates with said displaying means to query whether display of the image the content of which is summarized by said displayed summary information is desired, cooperates with said first inputting means to input an affirmative query response if the display of said image is desired, and selectively cooperates with said second read/write means and said displaying means to read the block of image information from said second memory means and to effect display of same only in response to the input of said affirmative query response.

* * * * *